US006645732B2

(12) United States Patent
Faatz et al.

(10) Patent No.: US 6,645,732 B2
(45) Date of Patent: *Nov. 11, 2003

(54) ANTIGEN-SPECIFIC IGG DETECTION

(75) Inventors: Elke Faatz, Huglfing (DE); Urban Schmitt, Oberhausen (DE)

(73) Assignee: Roche Diagnostics GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/319,080
(22) PCT Filed: Nov. 26, 1997
(86) PCT No.: PCT/EP97/06582
 § 371 (c)(1),
 (2), (4) Date: Nov. 8, 1999
(87) PCT Pub. No.: WO98/23961
 PCT Pub. Date: Jun. 4, 1998

(65) Prior Publication Data
US 2001/0006824 A1 Jul. 5, 2001

(30) Foreign Application Priority Data
Nov. 29, 1998 (DE) .......................... 196 49 390

(51) Int. Cl.⁷ .............................................. G01N 33/53
(52) U.S. Cl. ........................ 435/7.5; 435/7.1; 435/7.9; 435/7.92; 435/7.94; 435/965; 436/512; 436/513; 436/518; 530/866
(58) Field of Search .................... 435/7.1, 7.5, 7.9, 435/7.92, 7.94, 965; 436/512, 513, 518; 530/866

(56) References Cited

U.S. PATENT DOCUMENTS

| 4,292,403 | A |   | 9/1981  | Duermeyer ............... 435/5 |
|-----------|---|---|---------|-------------------------------|
| 4,929,543 | A | * | 5/1990  | Kientsch-Engel et al.         |
| 5,254,458 | A |   | 10/1993 | Mimms .................... 435/5 |
| 5,776,702 | A | * | 7/1998  | Schmitt et al.                |

FOREIGN PATENT DOCUMENTS

| EP |   0 186 799 A1 | 7/1986  | .......... G01N/33/52  |
| EP |   0 280 211 A2 | 8/1988  | ......... G01N/33/543  |
| EP |   0 307 149 A2 | 3/1989  | ......... G01N/33/543  |
| EP |   0 341 439 A1 | 11/1989 | ......... G01N/33/576  |
| EP |   0 386 713 A2 | 9/1990  | ......... G01N/33/569  |
| EP |   0 627 625 A1 | 12/1994 | ......... G01N/33/558  |
| WO |     90/08957   * | 8/1990  |                        |
| WO |   WO 96/14338   | 5/1996  | ........... C07K/16/00 |

OTHER PUBLICATIONS

Illustrated Dictionary of Immunology, 1995.*
Stedman's Medical Dictionary, 1995.*

* cited by examiner

Primary Examiner—Bao-Thuy L. Nguyen
(74) Attorney, Agent, or Firm—Marilyn L. Amick; Roche Diagnostics Corporation

(57) ABSTRACT

The invention concerns a method for the determination of antigen-specific antibodies of the immunoglobulin G class in the presence of immunoglobulins of the M class in body fluids by incubation with at least two different receptors $R_1$ and $R_2$ and optionally additional receptors, an essential component of $R_2$ being a binding partner in monomeric form, a reagent for determining an antigen-specific antibody of the immunoglobulin G class as well as the use of binding partners in monomeric form for the determination of an antigen-specific antibody of the immunoglobulin G class.

9 Claims, No Drawings

ANTIGEN-SPECIFIC IGG DETECTION

The invention concerns a method for the determination of antigen-specific antibodies of the immunoglobulin G class in body fluids by incubating the sample with at least two different receptors $R_1$ and $R_2$ wherein both receptors are capable of binding specifically to the antibody, $R_1$ is bound or can be bound to a solid phase and $R_2$ carries a label, separating the solid from the liquid phase and measuring the label wherein a conjugate of a binding partner in monomeric form which is specifically recognized by the antibody to be determined and a label is used as $R_2$.

In particular the invention concerns a method for the specific detection of immunoglobulins of the IgG class in the presence of immunoglobulins of the IgM class.

In response to the introduction of foreign substances the immune system of a mammalian organism produces antibodies which are also called immunoglobulins. They defend against foreign substances which are also referred to as antigens. The immunoglobulins can be divided into five different classes. One distinguishes between immunoglobulins of the M, G, A, E and D classes. Each of these five immunoglobulin classes differ in the composition of the heavy chain which is referred to as the $\mu$, $\gamma$, $\alpha$, $\epsilon$ and $\delta$ chain.

Each immunoglobulin class has a different function in the organism. Immunoglobulins of the M class appear with the first contact with the antigen the so-called first immunization. However, the concentration of these immunoglobulins decreases rapidly as the infection progresses. The immunoglobulins of the G class are firstly slowly formed after a first immunization and occur in large quantities when there is a second infection with the same antigen. The immunoglobulins of the A class are found on the mucous membrane surfaces of the organism and are responsible for the defence processes there. The immunoglobulins of the E class are mainly responsible for allergic reactions. The exact function of immunoglobulins of the D class is hitherto unknown.

The individual immunoglobulin classes occur in very different concentrations in the blood. Thus immunoglobulins of the G class (IgG) are the major class in normal human serum with a share of about 75% that corresponds to a serum content of 8 to 18 mg/ml. The second most frequently occurring immunoglobulin is IgA which has an average serum concentration of 0.9 to 4.5 mg/ml. Immunoglobulins of the M class are present at a concentration of 0.6 to 2.8 mg/ml, immunoglobulins of the D class are present at a concentration of 0.003 to 0.4 mg/ml. The proportion of IgE antibodies is lowest which only occur at a concentration of 0.02 to 0.05 µg/ml in serum.

For the differential diagnosis of many diseases it is important to detect antibodies of one or several quite particular immunoglobulin classes which are specific for a particular antigen. A satisfactory diagnosis of viral, bacterial and parasitic infections can only be ensured by means of a class-specific antibody test or by excluding the presence of certain immunoglobulin classes (e.g. detection of IgG and IgA antibodies but no detection of IgM antibodies). This is particularly important for the differentiation between fresh or acute infections and infections that have occurred earlier as well as for the clinical monitoring of the course of an infection. The class-specific detection of antibodies is especially important for HIV, hepatitis A, hepatitis B, toxoplasmosis, rubella and chlamydia infections. The class-specific detection of antibodies specific for a particular antigen is also necessary for the determination of the titre of protecting antibodies and to check the success of an immunization. Hence from a diagnostic view point there is great interest in the detection especially of antibodies of the non-acute stages of infections such IgG and IgA antibodies.

Various methods have been described in the state of the art for detecting antibodies of a particular class that are specific for an antigen. Hence antigen-specific antibodies of a particular class are frequently detected by binding the specific antibodies to a solid phase coated with the specific antigen. The immunoglobulins (Ig) specific for the antigen which are now bound to the solid phase are detected by binding antibodies which are specifically directed towards human Ig of a certain class to the Ig molecules to be detected. The antibodies directed towards human Ig are provided with a label by means of which the detection takes place. However, such a test procedure is only possible if all unspecific non-bound Ig is removed by washing before the reaction with the class-specific labelled antibodies directed towards human Ig. Thus a one-step test procedure as is often required for automated systems is not possible.

According to the method described in the U.S. Pat. No. 4,292,403 antigen-specific antibodies of a particular immunoglobulin class are detected by immobilizing a class-specific antibody on a solid phase which binds sample antibodies to be determined, subsequently adding the specific antigen and binding the bound antigen to a further labelled antibody that is specific for the antigen. However, a disadvantage of this method is that all antibodies of the class to be determined must bind to the class-specific immobilized antibody. The sample antibodies are not bound antigen-specifically. This could impair the sensitivity of the test since there may not be sufficient free binding sites for the antigen-specific antibody. Several wash steps are also necessary in this test procedure. This method does not enable a one-step test procedure.

One possibility of carrying out an antibody detection in a one-step test is provided by the so-called bridge test. The bridge test concept is described in EP-A-0 280 211. In this method a first receptor which is capable of specific binding to the antibody to be determined is bound to a solid phase such as for example an antigen. The antibody to be determined binds to the solid phase-bound antigen. In addition a further specific antigen is present in the test mixture which is provided with a label. The antibody is detected by means of the label. In this test all antigen-specific antibodies are detected and not only the antibodies of a particular class.

In EP-A-0 307 149 and in the U.S. Pat. No. 5,254,458 methods based on the bridge test principle are disclosed for the detection of antibodies which are directed specifically towards an antigen. In this case peptides produced recombinantly which are derived from a certain epitope of the antigen are used to bind the antibody to be detected. A peptide is immobilized to a solid phase. The sample antibody binds to the peptide. A further labelled peptide is bound to the sample antibody for the detection. The recombinant peptides are expressed in different organisms in order to increase the specificity of the test. Also in this method antibodies of all classes bind to the peptides. It is not possible to for example differentiate between IgG and IgM antibodies.

EP-A-0 386 713 describes a method for the detection of antibodies against HIV using two solid carriers in which different HIV antigens are immobilized on both solid carriers which are each contacted with an aliquot of a sample and a labelled HIV antigen wherein the presence of antibodies is detected by a positive reaction in at least one of the tests. Polypeptides produced recombinantly are disclosed as HIV antigens. A method based on Western blot is disclosed in EP-A-0 627 625 in which HIV antibodies can also be detected by means of recombinant proteins or synthetic peptides. However, both methods do not allow the class-specific detection of antigen-specific antibodies.

The previous methods do not enable an antigen-specific antibody of a certain immunoglobulin class to be detected in a one-step method. The immunological methods of detection known from the state of the art based on the bridge test concept in which a labelled antigen and an antigen capable of binding to a solid phase are used, do indeed enable a one-step test. However, up to now it has only been possible to jointly detect antibodies of the IgG and IgM classes using this simple principle.

Therefore the object was to provide an improved method for the detection of antibodies of a non-acute infection directed towards a specific antigen i.e. in particular of the IgG class. At the same time the method should ensure that IgM antibodies of the same specificity are not detected. This method should preferably consist of a one-step test principle in order to be used advantageously in automated systems.

This object is achieved by the method according to the invention for the determination of an antigen-specific antibody of the immunoglobulin G class by incubating the sample with at least two different receptors $R_1$ and $R_2$ wherein both receptors are capable of specifically binding to the antibody, $R_1$ is bound or can be bound to a solid phase and $R_2$ carries a label which is characterized in that a conjugate of a binding partner in monomeric form that is specifically recognized by the antibody to be determined and a label is used as $R_2$.

The method according to the invention allows the determination of antigen-specific antibodies of the immunoglobulin G class in samples in which antibodies of the IgM class of the same antigen-specificity are present.

The IgA, IgD and IgE antibodies present in the sample which have the same specificity as the IgG antibodies to be detected occur in much lower concentrations than the IgG antibodies. In particular the IgD and IgE classes are present in concentrations that are several orders of magnitude below the IgG concentration so that their reactivity in the detection method does not or hardly changes the measured result. IgA antibodies are present at concentrations that correspond to about 10% of the total IgG content. Hence IgA antibodies would also presumably be determined in this method. Since the main purpose of the method is to detect antibodies of the non-acute infection, the joint detection of IgG and IgA antibodies which are both antibodies of the non-acute infection is not critical. Since IgG antibodies are the major immunoglobulin class in the non-acute infection the term IgG detection is used in the following. It is essential that IgM antibodies of the same antigen specificity which only occur in large quantities in an acute infection must not be detected.

It has surprisingly turned out that the use according to the invention of binding partners in a monomeric form in a bridge test based on the double-antigen test principle enables antibodies of the IgG class to be exclusively detected which are specifically directed towards a particular antigen. Antibodies of the IgM class of the same specificity which are present in the same sample surprisingly do not react or only to a negligibly weak extent with monomeric peptides and thus do not interfere with the IgG detection. The term "negligibly weak" means that the antigen binding sites of the IgM antibodies are not detectably bound by the binding partners in monomeric form. This is presumably due to the much lower affinity of the pentameric IgM antibodies for monomeric epitopes compared to the IgG antibodies present in the form of individual molecules.

Hence a successive test procedure for separating the IgM antibodies is not absolutely necessary in the method according to the invention since these do not interfere. A particular advantage of the method is therefore the simplicity of the test procedure.

Apart from the so-called wet tests in which the test reagents are present in a liquid phase, all standard dry test formats which are suitable for the detection of proteins or antibodies can also be used. In these dry tests or test strips as described for example in EP-A-0 186 799, the test components are applied to a carrier. Hence if the method according to the invention is carried out in a test strip format no wash step is necessary. However, the method according to the invention is preferably carried out as a wet test.

It is possible to incubate all receptors and the sample together and to carry out the method in one step. This optionally requires only one wash step after the incubation.

Normally two different receptors $R_1$ and $R_2$ are used to carry out the method according to the invention. If a wet test is used, the receptor $R_2$ is present in a liquid phase. $R_1$ can be present in a liquid phase or already bound to the solid phase. If $R_1$ and $R_2$ are present in a liquid phase, they are preferably at the same concentration. Concentration ratios of $R_1$:$R_2$ of 0.5:1.0 to 1.0:5.0 have proven to be well suited. The optimal concentration ratios can easily be tested out by a person skilled in the art.

If a receptor capable of binding to a solid phase but which is not yet bound to the solid phase is used as $R_1$, the sample is then incubated with the receptors $R_1$ and $R_2$. In this process the sample antibody binds to $R_1$ and $R_2$. This incubation can occur in the presence of the solid phase. A complex is formed in this process comprising solid phase-$R_1$-sample-antibody-$R_2$.

Subsequently the solid phase is separated from the liquid phase, the solid phase is optionally washed and the label of $R_2$ is measured. The label is usually measured in the solid phase it can, however, also be determined in the liquid phase.

If the incubation of the sample with $R_1$ and $R_2$ is carried out in the absence of the solid phase, then the entire test mixture must subsequently be contacted with the solid phase, the washing optionally carried out and the label measured.

If the receptor $R_1$ is already in a solid phase-bound form, then the sample and receptor $R_2$ are added to the solid phase-bound receptor $R_1$ and incubated together. The further procedure corresponds to the process stated above.

It is, however, also possible to carry out the method according to the invention in several steps. In this case it is expedient to firstly incubate the sample with the receptors $R_1$ and $R_2$. The complex of $R_1$, $R_2$ and antibody to be determined that is formed is subsequently incubated with other receptors whereby this can be carried out in several steps. The further test procedure corresponds to the previously described method.

The receptor $R_2$ is a conjugate of a binding partner in monomeric form and a label. The binding partners according to the invention in monomeric form contain exactly one epitope region or only one binding site for the antibody to be determined i.e. a structure that reacts immunologically specifically with the IgG antibody to be determined. The monomeric structure of the binding partner is important to ensure that only the antigen-specific IgG antibodies to be detected bind to the binding partner in monomeric form and not the interfering IgM antibodies of the same specificity.

The epitope region can for example be derived from an antigen or an anti-idiotype antibody. The epitope regions can, in the case of the binding partners in monomeric form, also be derived from sugar and/or lipid structures or combined structures with peptide, lipid and/or sugar components. All structures that can be derived from an epitope region can be used which have a binding site to which the antibody of the IgG class to be detected specifically binds in the presence of IgM antibodies of the same specificity. The only prerequisite for the binding site i.e. for the binding partners used in monomeric form, is that the specific capability of binding to IgG is retained. This condition also applies to the case where sugar or lipid structures are present in the binding site.

According to the invention it is also possible to use binding partners in monomeric form which flank or overlap with the binding site to which the IgG antibody to be detected specifically binds. Hence it is also possible to detect cross-reacting IgG antibodies whose binding site overlaps with the epitope to be detected. Therefore a mixture of binding partners in monomeric form is preferably used to detect the antigen-specific IgG antibodies.

Peptides are preferably used as binding partners in monomeric form. In the case of a protein as an analyte a binding site is understood as a peptide, the sequence of which is part of the protein sequence of a protein antigen and to which an antibody directed towards this protein, which in the case of the present invention is an IgG antibody, specifically binds. In addition to these peptides a binding site is also understood to include peptides with amino acid sequences which have an essentially equivalent specificity and/or affinity of binding to the IgG antibody to be detected as the aforementioned peptides. These peptides can preferably be derived from the aforementioned peptides by substitution, deletion or insertion of individual amino acid residues.

All peptides can be used which have a binding site to which the IgG class antibody to be determined bind specifically even in the presence of IgM antibodies of the same specificity. The only prerequisite for the binding site i.e. for the peptide used, is that its ability to specifically bind to IgG is retained. A binding site is understood as a peptide whose sequence is part of the protein sequence of a protein antigen (analyte) and to which an antibody directed against this protein specifically binds which in the present invention is an IgG antibody. In addition to these peptides a binding site is also understood to include peptides with amino acid sequences which have an essentially equivalent specificity and/or affinity of binding to the IgG antibody to be determined as the aforementioned peptides. These peptides can preferably be derived from the aforementioned peptides by substitution, deletion or insertion of individual amino acid residues.

Peptides according to the invention which correspond to a specific binding site are also understood to include peptide derivatives in which one or several amino acids have been derivatized by a chemical reaction. Examples of peptide derivatives according to the invention are in particular those molecules in which the backbone or/and reactive amino acid side groups, for example free amino groups, free carboxyl groups or/and free hydroxyl groups, have been derivatized. Specific examples of derivatives of amino groups are sulfonamides or carboxamides, thiourethane derivatives and ammonium salts for example hydrochlorides. Carboxyl group derivatives are salts, esters and amides. Examples of hydroxyl group derivatives are O-acyl or O-alkyl derivatives. The peptides are preferably produced by chemical synthesis according to methods known to a person skilled in the art and do not need to be especially elucidated here. In principle the peptides can also be produced by means of recombinant methods. However, longer polypeptides often tend to dimerize or polymerize so that the peptides are preferably produced by chemical synthesis in order to ensure monomeric properties.

In addition the term peptide derivative also encompasses such peptides in which one or several amino acids are replaced by naturally occurring or non-naturally occurring amino acid homologues of the 20 "standard" amino acids. Examples of such homologues are 4-hydroxyproline, 5-hydroxylysine, 3-methylhistidine, homoserine, ornithine, β-alanine and 4-aminobutyric acid. The peptide derivatives must have an essentially equivalent specificity or/and affinity of binding to the IgG antibodies to be determined as the peptides from which they are derived.

Peptides according to the invention which correspond to a specific binding site are also referred to as peptide-mimetic substances named peptide-mimetics in the following which have an essentially equivalent specificity or/and affinity of binding to the IgG antibodies to be determined as the aforementioned peptides or peptide derivatives. Peptide-mimetics are compounds which can replace peptides with regard to their interaction with the antibody to be determined and can have a higher stability than the native peptides in particular towards proteinases and peptidases. Methods for the production of peptide-mimetics are described in Giannis and Kolter, "Angew. Chem." 105 (1993), 1303–1326 and Lee et al., Bull. Chem. Soc. Jpn. 66 (1993), 2006–2010.

The length of a binding site i.e. the length of a monomeric peptide according to the invention is usually at least 4 amino acids. The length is preferably between 4 and 20, 6 and 15 or particularly preferably 9 and 12 amino acids. In the case of peptide-mimetics or peptide derivatives an analogous length is necessary with regard to the size of the molecule.

The monomeric peptides according to the invention as a binding partner in a monomeric form contain the epitope to which the IgG antibody to be determined binds specifically. However, further flanking peptide sequences which no longer correspond to the specific epitope may be present at the N-terminal and/or at the C-terminal end of the peptide. Furthermore it is possible that the peptide is provided with spacer groups familiar to a person skilled in the art. The only prerequisites are that the peptide as a binding partner in a monomeric form is actually present as a monomer and the ability to bind to the IgG antibodies to be determined is retained.

A further component of the receptor $R_2$ is the label. A directly detectable substance is preferably used as a label for example a chemiluminescent, fluorescent or radioactive substance or a metal sol, latex or gold particle. Enzymes or other biological molecules are also preferred as the label such as for example haptens. Digoxigenin is a particularly preferred label among the haptens. Processes for labelling are familiar to a person skilled in the art and do not need to be elucidated further here. The label is detected directly in a well-known manner by measuring the chemiluminescent, fluorescent or radioactive substance or the metal sol, latex or gold particle or by measuring the substrate converted by the enzyme.

The label can also be detected indirectly. In this case a further receptor which itself is in turn coupled to a signal-generating group binds specifically to the label of $R_2$ such as a hapten such as digoxigenin. The signal-generating group for example a chemiluminescent, fluorescent or radioactive substance or an enzyme or gold particle is detected by methods familiar to a person skilled in the art. An antibody or an antibody fragment can for example be used as the further receptor which binds specifically to the label of $R_2$. If this indirect detection of the label is used then the $R_2$ label is preferably digoxigenin or another hapten and the detection is carried out via an antibody coupled to peroxidase which is directed towards digoxigenin or towards the hapten.

An essential component of the receptor $R_1$ is a binding partner which is capable of specific binding to the IgG antibody to be determined. The receptor $R_1$ can be directly bound to the solid phase or capable of binding to the solid phase. A binding partner in a monomeric form as in receptor $R_2$ can be used as the binding partner which is capable of specific binding to the IgG antibody to be determined. However, it is also possible to use binding partners which are not present in a monomeric form i.e. the binding partner can have more than one epitope or binding site. It is important that the ability of the binding partner to specifically bind to the IgG antibodies to be determined is retained. However, binding partners in a monomeric form and particularly preferably peptides are also used for the receptor $R_1$. The peptides contained in $R_1$ are produced by the same methods as the peptides for $R_2$.

The antibody-specific binding partners or peptides contained in the receptors $R_1$ and $R_2$ may be identical or different, but both must be capable of simultaneously binding to the IgG antibody to be determined.

$R_1$ can either be bound directly to the solid phase. The direct binding of $R_1$ to the solid phase is achieved by methods known to a person skilled in the art. $R_1$ can also be indirectly bound to the solid phase by means of a specific binding system. In this case $R_1$ is a conjugate which is composed of a peptide as elucidated above and a reaction partner of a specific binding system. A specific binding system is in this case understood as two partners which can react specifically together. In this case the binding capability can be based on an immunological reaction or on another specific reaction. A combination of biotin and avidin or biotin and streptavidin is preferably used as a specific binding system. Other preferred combinations are biotin and antibiotin, hapten and anti-hapten, Fc fragment of an antibody and antibody against this Fc fragment or carbohydrate and lectin. One of the reaction partners of this specifically bindable pair is then a part of the conjugate that forms the receptor $R_1$.

The other reaction partner of the specific binding system is then present in a solid phase. The other reaction partner of the specific binding system can be bound to an insoluble carrier material by conventional methods known to a person skilled in the art. In this case a covalent as well as an adsorptive binding is suitable. Solid phases that are particularly suitable are test tubes or microtitre plates made of polystyrene or similar plastics the inner surfaces of which are coated with the reaction partner of the specific binding system. Particulate substances such as latex particles, molecular sieve materials, glass beads, plastic tubes etc. are also suitable and particularly preferred. Porous layered carriers such as paper can also be used as the carrier.

In a preferred embodiment of the method according to the invention a conjugate composed of a binding partner in a monomeric form and a reaction partner of the specific binding system is used as $R_1$. In this preferred embodiment the receptors $R_1$ and $R_2$ as well as the sample which contains the IgG antibody to be determined are incubated together. In this process the peptide components of the receptors $R_1$ and $R_2$ react specifically with the IgG antibodies to be determined. This complex composed of $R_1$, sample antibody and $R_2$ is bound to the solid phase which is coated with the other reaction partner of the specific binding system by means of the reaction partner of the specific binding system which is a component of $R_1$. As a result the entire complex composed of $R_1$, sample antibody and $R_2$ is bound to the solid phase. After the solid phase has been separated from the liquid phase and optionally washing the solid phase, the label of $R_2$ is detected by methods known to a person skilled in the art. This test procedure enables IgG antibodies to be detected specifically in the presence of IgM antibodies of the same specificity.

In a further preferred embodiment of the method according to the invention an additional receptor is used in addition to the receptors $R_1$ and $R_2$. In this test procedure a conjugate composed of a binding partner in monomeric form and a reaction partner of a specific binding system such as for example biotin is used as $R_1$. For this the receptors $R_1$ and $R_2$ as well as the sample which contains the IgG antibody to be determined are incubated together. In this process the peptide components of the receptors $R_1$ and $R_2$ react specifically with the IgG antibodies to be determined. Binding to the solid phase which is coated with the other reaction partner of the specific binding system (for example with streptavidin) is achieved by means of the one reaction partner of a specific binding system that is a component of $R_1$. As a result the entire complex composed of $R_1$, $R_2$ and sample antibody is bound to the solid phase. After separating the solid phase from the liquid phase and optionally washing the solid phase, the complex bound to the solid phase is incubated with an additional receptor which specifically recognizes the label of $R_2$. The further receptor is coupled to a signal-generating group such as an enzyme. After a further optional washing step, the sample antibody is detected via the signal-generating group, in this case by the substrate converted by the enzyme. If this test procedure is used digoxigenin is preferably used as the $R_2$ label. The additional receptor in this case is composed of an antibody or antibody fragment directed towards digoxigenin and the enzyme peroxidase. In this test procedure the incubation of the sample with $R_1$ and $R_2$ and the additional receptor can also be carried out concurrently.

This test procedure is also very well suited for an application to automated systems but requires two or several washing steps. A major advantage of this test procedure becomes apparent if it is intended to detect several antigen-specific antibodies such as e.g. HIV antibodies against gp41, p17 etc. In such a case the additional receptor can be used as a universal label since this additional receptor specifically recognizes the $R_2$ label.

All biological liquids known to a person skilled in the art can be used as samples. Body fluids such as whole blood, blood serum, blood plasma, urine, saliva etc. are preferably used as the sample.

In addition to the sample, the solid phase and the aforementioned receptors, other additives which may be required depending on the application such as buffer, salts, detergents, protein additives such as BSA may be present in the test mixtures. The necessary additives are known to a person skilled in the art or can be determined by him in a simple manner.

In order to ensure that IgM antibodies or rheumatoid factors do not interfere with the antigen-specific IgG detection, it is possible to optionally use additional measures for interference reduction. These for example include the use of reducing substances such as dithiothreitol (DTT), dithioerythritol (DTE) or β-mercaptoethanol in the approach disclosed in EP-B-0 341 439. In addition anti-Fd antibodies can optionally be used to eliminate interference by rheumatoid factors. Such a concept is disclosed in WO 96/14338. The various measures for reducing interference can be used individually or in any combination.

A further subject matter of the invention is a reagent for the determination of an antigen-specific antibody of the immunoglobulin G class which, in addition to the usual test additives for immunoassays such as buffers, salts, detergents etc., contains a receptor $R_2$ capable of binding to the antibody to be determined which is composed of a binding partner in a monomeric form and a label.

A subject matter of the invention is also a reagent for the determination of an antigen-specific antibody of the immunoglobulin G class which, in addition to the usual test additives for immunoassays, contains two receptors $R_1$ and $R_2$ capable of binding to the antibody to be determined of which $R_1$ is capable of binding to a solid phase and $R_2$ carries a label wherein an essential component of receptor $R_2$ is a binding partner in a monomeric form.

A further subject matter of the invention is also a reagent for the determination of an antigen-specific antibody of the immunoglobulin G class which, in addition to the usual test additives for immunoassays, contains two receptors $R_1$ and $R_2$ capable of binding to the antibody to be determined of which $R_1$ is capable of binding to a solid phase and $R_2$ carries a label wherein an essential component of both receptors is a binding partner in a monomeric form.

Furthermore a subject matter of the present invention is the use of binding partners in a monomeric form to determine an antigen-specific antibody of the immunoglobulin G class.

The invention is elucidated by the following examples.

EXAMPLES

1. Reactivity with <HIV 2>MABs (IgG and IgM) when using Monomeric and Multimeric Epitopes Description of the Test Procedure Biotin-labelled and digoxigenin-labelled monomeric (test A) or multimeric (test B) antigens (HIV 2) react with sample antibodies and a streptavidin-coated solid phase (incubation at 25° C. or 37° C., ca. 60 to 180 min, in this example: 120 min, 25° C.). After a wash step the immune complex bound to the wall reacts with an anti-digoxigenin-peroxidase conjugate (incubation at 25° C. or 37° C., ca. 30 to 120 min in this example: 60 min 25° C.). After a further wash step the peroxidase conjugate-labelled immune complex is detected by a substrate reaction (conjugate incubation 60 min at 25° C.). In general the conjugate incubation can be carried out at 25° C. or 37° C., for ca. 30 to 120 min.

The reaction steps (apart from the substrate reaction) take place in a Tris/HCl buffer (pH 7.5, 50 to 150 mM in this example 100 mM) containing ca. 0.05 to 0.4% detergent (here 0.2% polidocanol) and ca. 0.5% protein/protein derivative additives (here peptone from lactalbumin and BSA among others).

In this case the sample antibodies are monoclonal mouse antibodies (IgM and IgG) against a HIV 2 epitope diluted to ca. 2–20 µg/ml in anti-HIV negative human serum.

TABLE 1

Test results comparison of tests A and B: Absorbances in mA

| Samples | Test A (monomeric epitopes) | Evaluation | Test B (multimeric epitopes) | Evaluation |
|---|---|---|---|---|
| MAB < HIV2 > IgG 20.3.1 | 2764 | positive | 2800 | positive |

TABLE 1-continued

Test results comparison of tests A and B: Absorbances in mA

| Samples | Test A (monomeric epitopes) | Evaluation | Test B (multimeric epitopes) | Evaluation |
|---|---|---|---|---|
| MAB < HIV2 > IgG 23.5.3 | 9999 | positive | 3974 | positive |
| MAB < HIV2 > IgM 2.6.6 | 6 | negative | 3271 | positive |
| MAB < HIV2 > IgM 2.11.7 | 6 | negative | 4250 | positive |
| MAB < HIV2 > IgM 2.22.8 | 6 | negative | 6442 | positive |

The use of HIV2-specific binding partners in a monomeric form enables the specific detection of IgG antibodies against HIV2. Antibodies of the IgM class of the same antigen specificity are not recognized (test A).

When HIV2-specific binding partners in a multimeric form are used it is not possible to discriminate between IgG and IgM (test B).

2. Reactivity with Serum Antibodies of a HIV2 Seroconversion of a Chimpanzee

Experimental procedure as example 1.

TABLE 2

Test results of a chimpanzee seroconversion with tests A and B: Absorbances in mA

| Sequential serum samples after infection | Test A (monomeric epitopes) | Evaluation | Test B (multimeric epitopes) | Evaluation |
|---|---|---|---|---|
| week 0 (on infection) status: no antibodies | 6 | negative | 98 | negative |
| week 1 after infection status: no antibodies | 7 | negative | 89 | negative |
| week 3 after infection status: IgM antibodies | 6 | negative | 673 | positive |
| week 7 after infection status: IgM and IgG antibodies | 250 | borderline | 589 | positive |
| week 10 after infection status: IgG antibodies | 8767 | positive | 6845 | positive |

The use of binding partners in a monomeric form enables the seroconversion after a HIV2-infection to be detected. The advantage of test A is particularly apparent in week 3 after the infection: only IgM antibodies are present which are not detected by the binding partners in a monomeric form. Test A only shows a positive signal after IgG antibodies appear. Test B which uses multimeric epitopes is not able to distinguish between IgG and IgM of the same specificity.

3. Reactivity with Serum Antibodies of a HIV1 Seroconversion of a Patient

Experimental procedure as example 1, but antigens of HIV 1.

TABLE 3

Test results of a HIV1 seroconversion with tests A and B
Adsorbances in mA

| Sequential serum samples after the first examination | Test A (monomeric epitopes) | Evaluation | Test B (multimeric epitopes) | Evaluation |
|---|---|---|---|---|
| day 0 status: no antibodies | 30 | negative | 89 | negative |
| day 14 status: no antibodies | 28 | negative | 78 | negative |
| day 26 status: IgG antibodies | 35 | negative | 9999 | positive |
| day 35 status: IgM and IgG antibodies | 250 | borderline | 9999 | positive |
| day 40 status: IgM and IgG antibodies | 589 | positive | 9151 | positive |

Test A enables a reliable detection of IgG antibodies also in the case of an infection with HIV1 (analogous to HIV2 according to example 2).

4. Detection of IgG Against Rubella with Peptides that Contain Monomeric Epitopes Description of the Test Procedure Rubella-specific IgG is detected by means of the binding partners according to the invention in a monomeric form on an Elecsys® 2010 instrument from Boehringer Mannheim GmbH, Germany according to the manufacturer's instructions. The following reagents are used:

Reagent R1: cyclic peptide of rubella E1 antigen, biotinylated. Tris buffer, pH 7.5, 0.2% Myrij, 0.2% BSA, 0.1% R-IgG Reagent R1: cyclic peptide of rubella E1 antigen, ruthenylated. Tris buffer, pH 7.5, 0.2% Myrij, 0.2% BSA, 0.1% R-IgG.

Human serum samples are used as samples.

The test is carried out in the following steps:
1. 30 µl sample+65 µl $R_1$+65 µl $R_2$
2. incubation at 37° C., 9 min
3. addition of 40 µl SA-coated magnetic beads
4. incubation at 37° C., 9 min
5. detection reaction: measuring the electrochemiluminescent signal

TABLE 4

| Samples | Characterization | counts | IU/ml |
|---|---|---|---|
| No. 1 | IgM neg., IgG neg. | 1359 | 0.5 |
| No. 3 | IgM neg., IgG neg. | 1370 | 0.5 |
| No. 8 | IgM neg., IgG neg. | 1338 | 0.5 |
| No. 1.3 | IgM pos., IgG neg. | 929 | 0.1 |
| No. 1.4 | IgM pos., IgG neg. | 981 | 0.2 |
| No. 255 | IgM neg., IgG pos. | 11256 | 83 |
| No. 272 | IgM neg., IgG pos. | 26254 | 192 |

TABLE 4-continued

| Samples | Characterization | counts | IU/ml |
|---|---|---|---|
| No. 278 | IgM neg., IgG pos. | 4453 | 32 |
| No. 283 | IgM neg., IgG pos. | 49328 | 363 |

Only samples which contain antigen-specific IgG are recognized as positive. Samples which only contain antigen-specific IgM (No. 1.3 and 1.4) are not recognized according to the invention as positive.

What is claimed is:

1. A method for the determination of an antigen-specific antibody of the immunoglobulin G class in a biological sample comprising the steps of:

a. forming a mixture by combining said sample with at least two different receptors, $R_1$ and $R_2$, in which each of said receptors binds specifically to said antibody via its antigen-binding site according to the double antigen test principle, $R_1$ is bound to a solid phase and $R_2$ comprises a conjugate of a binding partner in monomeric form and a label, thereby forming a complex comprising solid phase-$R_1$-antibody-$R_2$-label, characterized in that the sample is combined together simultaneously with $R_1$ and $R_2$ in one step, b. separating the solid phase complex from the mixture, and c. measuring said label bound to said antibody via $R_2$ as a measure of said antibody present in said sample.

2. The method of claim 1, wherein $R_1$ comprises a binding partner in monomeric form.

3. The method of claim 2, wherein the binding partner in monomeric form comprising $R_1$ is present in an amount greater than or the same as the amount of binding partner in monomeric form comprising $R_2$.

4. The method of claim 1, wherein $R_1$ is bound to said solid phase by a specific binding system selected from the group consisting of biotin/avidin, biotin/streptavidin, biotin/antibiotin, hapten/antihapten, Fc fragment of an antibody/antibody against said Fc fragment, and carbohydrate/lectin.

5. The method of claim 1, wherein said label is selected from the group consisting of chemiluminescent, fluorescent and radioactive substances, enzymes and biological molecules.

6. The method of claim 1, wherein said mixture includes an additional receptor which specifically binds to said label, wherein said additional receptor comprises a conjugate of a receptor specific for said label and a second label, wherein said second label indirectly bound to said antibody is determined as a measure of said antibody present in said sample.

7. The method of claim 1, wherein said antibody is an HIV 2 antibody.

8. The method of claim 1, wherein said antibody is an HIV 1 antibody.

9. The method of claim 1, wherein said antibody is a rubella antibody.

* * * * *